US00PP13108P2

(12) United States Plant Patent
Olesen et al.

(10) Patent No.: US PP13,108 P2
(45) Date of Patent: Oct. 22, 2002

(54) ROSE PLANT NAMED 'POULRA005'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/780,137

(22) Filed: Feb. 8, 2001

(51) Int. Cl.[7] ..... A01H 5/00
(52) U.S. Cl. ..... Plt./122
(58) Field of Search ..... Plt./122

(56) References Cited

PUBLICATIONS

UPOV–ROM GTITM Computer Database, 2001/04, GTI Jouve Retrieval Software, citation for 'POULra005'.*

* cited by examiner

*Primary Examiner*—Bruce R. Campell
*Assistant Examiner*—Susan B. McCormick

(57) ABSTRACT

A new miniature rose plant which has abundant, red-orange flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

BOTANICAL CLASSIFICATION

*Rosa hybrida.*

VARIETY DENOMINATION

'POULra005'.

SUMMARY OF THE INVENTION

The present invention constitutes a new and distinct variety of miniature rose plant which originated from a controlled crossing between 'POULhappy' (U.S. Plant Pat. No. 9,483, issued Mar. 26, 1996) and 'Rumba', an unpatented variety. The two parents were crossed and the resulting seeds were planted in a controlled environment. The new variety is named 'POULra005'.

The new rose may be distinguished from its seed parent, 'POULhappy', by the following combination of characteristics:

1. The blooms of 'POULhappy' are red, whereas 'POULra005' blooms are bright red-orange.

2. The flowers of 'Poulra005' are larger than those of 'POULhappy'.

The new variety may be distinguished from its pollen parent, 'Rumba', an unpatented variety created by the same inventors, by the following combination of characteristics:

1. 'Rumba' has bi-color (yellow & red) blooms, whereas 'POULra005' has orange-red blooms.

2. 'Rumba' is used in commercial cut flower production, while 'POULra005' is used for forced pot plant production.

The objective of the hybridization of this rose variety for commercial culture was to create a new and distinct variety with unique qualities, such as:

1. Uniform and abundant red-orange flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

This combination of qualities is not present in previously available commercial cultivars of this type and distinguish 'POULra005' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULra005' was selected by the inventors as a single plant from the progeny of the hybridization in spring 1998.

Asexual reproduction of 'POULra005' by cuttings and traditional budding was first done by L. Pernille and Mogens N. Olesen in their nursery in Fredensborg, Denmark in June 1998. This initial and other subsequent propagations conducted in controlled environments have demonstrated that the characteristics of 'POULra005' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra005'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULra005', as observed in its growth in Burlington, Ontario, Canada on plants aged sixteen weeks. Root development for the observed plant typically takes 8 to 10 weeks. Color references are made using The Royal Horticultural Society (London, England) Colour Chart, 1995, except where common terms of color are used.

For a comparison, several physical characteristics of the rose variety 'POULhappy', a rose variety from the same inventors described and illustrated in U.S. Plant Pat. No. 9,486 and issued on Mar. 26, 1996 are compared to 'POULra005' in Chart 1.

CHART 1

| | 'POULra005' | 'POULhappy' |
|---|---|---|
| Petal color; after opening, inner side | Red Group 43A | Red Group 46B |
| Open bloom size | 45–55 mm | 25–30 mm |
| Petalage | 45–55 | 25–30 |

Parents: 'POULhappy'×'Rumba'.

Classification:

(*Genus, species, cultivar*).—*Rosa Hybrida* POULra005.

*Commercial.*—Miniature.

FLOWER AND FLOWER BUD

Blooming habit: Continuous.

Flower bud:

*Size.*—Upon opening, 20–22 mm in length from base of receptacle to end of bud.

*Bud form.*—Short and pointed ovoid.

*Bud color.*—As sepals unfold, Red Group 45B. Red Group 44A at ¼ opening.

*Sepals.*—Yellow-Green Group 144A. Moderate foliaceous appendages on 3 of the 5 sepals. Surfaces of sepals slightly pubescent. Limited number of stipitate glands are present along sepal margins. Sepals are 18–22 mm long and 5–7 mm wide.

*Receptacle.*—Surface: Smooth. Shape: Urn-shaped. Size: Small. 6 mm(h)×8 mm (w). Color: Yellow-Green Group 144A. Anthocyanin: None.

*Peduncle.*—Surface: Slightly pubescent with a moderate number of stipitate glands. Length: 24–26 mm average length. Color: Yellow-Green Group 146A. Strength: Erect.

*Borne.*—Multiple. (2–5) buds per stem.

Flower bloom:

*Fragrance.*—Moderate.

*Duration.*—As a pot plant, flowers last from 16 to 22 days. As a cut flower 4 to 6 days. The blooms have a duration on the plant of approximately 10 to 15 days.

*Size.*—Large for an 8–11 cm pot rose. Average flower diameter is 38–43 mm when open.

*Form.*—Shape of flower when viewed from the side: Upon opening, upper part: Flat. Upon opening, lower part: Flat. Open flower, upper part: Flat. Open flower, lower part: Flat.

*Petalage.*—Very double. Average range: 45–55 petals under normal conditions with 0–3 petaloids.

Color:

*Upon opening, petals.*—Outermost petals: Outer Side: Red Group 45B. Inner Side: Red Group 43A. Innermost petals: Outer Side: Red Group 53C. Inner Side: Red Group 45A. Inner petals occasionally exhibit narrow stripe of White Group 155B-C-D emanating from the basal zone to the middle zone of the petal.

*Upon opening, basal petal spots.*—Outermost petals: Outer Side: Green-Yellow Group 1C. Inner Side: White Group 155C. Innermost petals: Outer Side: Green-Yellow Group 1D. Inner Side: Yellow-Green Group 1C.

*After opening, petals.*—Outermost petals: Outer Side: Red Group 47B. Inner Side: Red Group 43A. Innermost petals: Outer Side: Red Group 50A. Inner Side: Red Group 43A.

*After opening, basal petal spots.*—Outermost petals: Outer Side: White Group 155C. Inner Side: Green-White Group 157D. Innermost petals: Outer Side: Yellow Group 1D. Inner Side: Yellow Group 1D.

General tonality: On open flower, Red Group 43A. No change in the general tonality at the end of the 12$^{th}$ day. Afterwards, general tonality is Red Group 43B–C.

Petals:

*Petal reflex.*—Somewhat.

*Petal edge.*—Entire.

*Shape.*—Deltoid; base is flat at union with receptacle.

*Petaloids.*—Present. Quantity: 0–3.

*Thickness.*—Average.

*Arrangement.*—Imbricated.

Reproductive organs:

*Pollen.*—Color: Greyed-Orange Group 164C. Quantity: Average.

*Anthers.*—Size: Small. Color: White Group 155C. Quantity: Average.

*Filaments.*—Color: Yellow Group 4A.

*Stigmas.*—Slightly superior in location to anthers. Color: Greyed-Yellow Group 160C.

*Styles.*—Color: Yellow-Green Group 145C.

*Seed formation.*—Hips not observed on pot plants.

PLANT

Plant growth: Vigorous, and compact. When grown as an 8–11 cm pot plant, the average height of the plant is 20–25 cm and the average width is 15–20 cm.

Stems:

*Color.*—Young wood: Green Group 143A. Older wood: Green Group 143A.

*Prickles.*—Incidence: Moderate. Size: Average length: 1–3 mm. Color: Greyed-Orange Group 163C. Shape: Concave.

*Surface.*—Young wood: Smooth. Older wood: Smooth.

*Length.*—Stem length is typically 20 to 25 cm.

*Diameter.*—Stem diameter is typically 4 to 6 mm.

Plant foliage: Typical number of leaflets on normal leaves in middle of the stem: 5 leaflets.

*Typical leaf size.*—Small. 90 mm (l)×60 mm (w).

*Quantity.*—Very abundant.

*Color.*—Upper Leaf Surface: Green Group 137A. Lower Leaf Surface: Green Group 138B. Juvenile foliage: Upper Leaf Surface: Yellow-Green Group 147A. Lower Leaf Surface: Yellow-Green Group 148B.

*Anthocyanin intonation.*—Location: On lower leaf surface of juvenile and mature foliage. Present on upper leaf surface on juvenile foliage. Color: Greyed-Purple Group 184B.

Plant leaves and leaflets:

*Stipules.*—Size: 8–10 mm (l)×3–5 mm (w). Color: Yellow-Green Group 144B. Presence of stipitate glands: Located along margins of stipules. Anthocyanin: None.

*Petiole.*—Length: 25–28 mm. Color: Yellow-Green Group 144A. Underneath: Typically smooth with occasional small prickle. Margins: Moderate number of stipitate glands. Anthocyanin: On upper surface margins of mature and juvenile foliage. Color: Greyed-Purple Group 183C.

*Rachis.*—Color: Yellow-Green Group 144B. Underneath: Smooth with occasional small prickle. Margins: Moderate number of stipitate glands. Anthocyanin: On upper surface margins of mature and juvenile foliage. Color: Greyed-Purple Group 183C.

*Leaflet.*—Edge: Serrated. Shape: Pointed, ovate. Other: Glossy and thin.

Disease resistance: Above average resistance to mildew, black spot, and Botrytis under normal growing conditions in Burlington, Canada.

Cold hardiness: 'POULra005' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant, red-orange flowers, vigorous growth, compact habit, suitability for production from softwood cuttings in pots, and durable flowers and foliage which make the variety suitable for distribution in the floral industry.

* * * * *

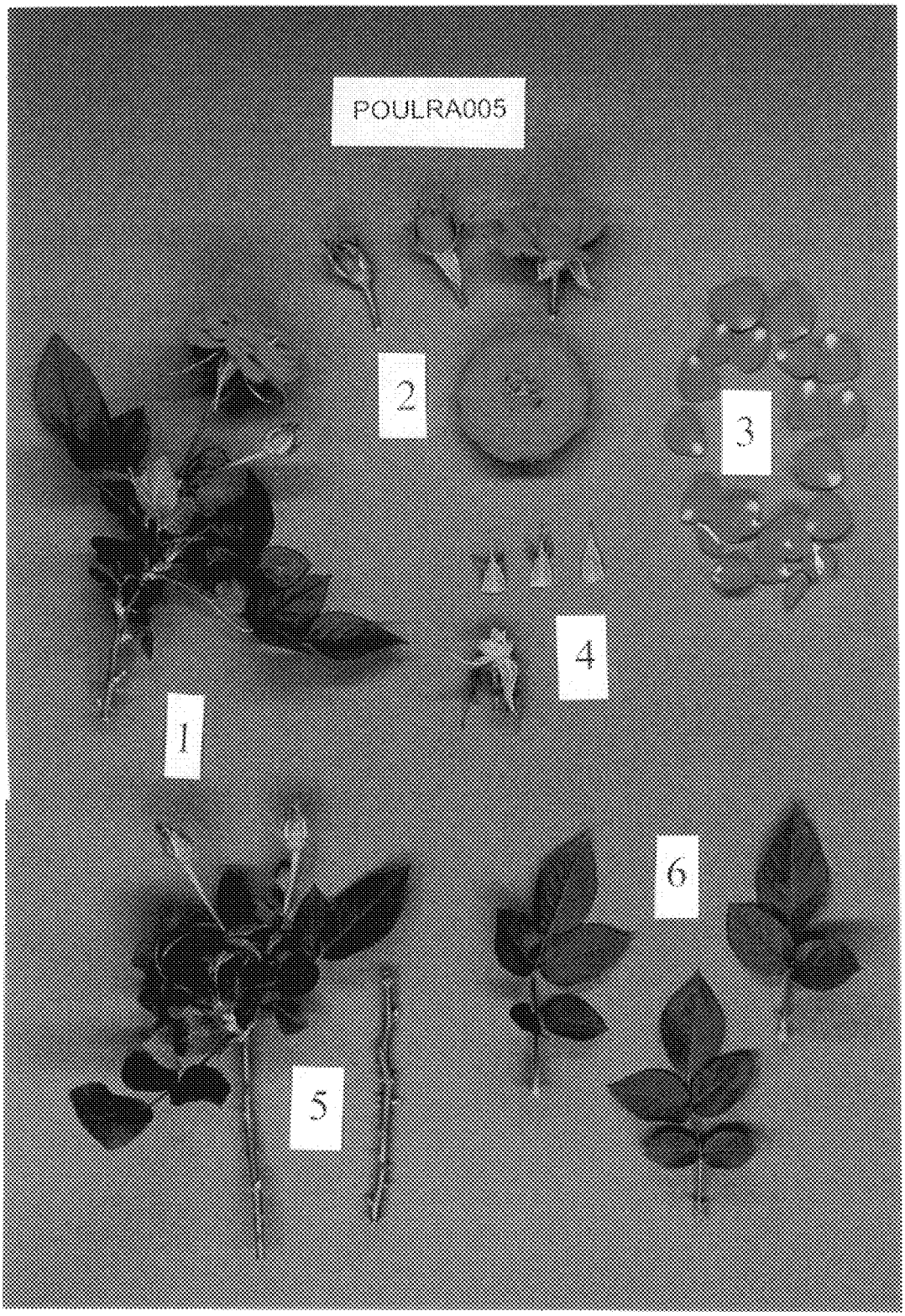
POULRA005
1
2
3
4
5
6